United States Patent [19]
Brady et al.

[11] Patent Number: 5,107,023
[45] Date of Patent: Apr. 21, 1992

[54] 0-AMINOPHENYL CYCLOPROPYL KETONE INTERMEDIATE

[75] Inventors: Thomas E. Brady, Hunterdon; Michael E. Condon, Mercer; Pierre A. Marc, Burlington, all of N.J.

[73] Assignee: American Cyanamid Company, Stamford, Conn.

[21] Appl. No.: 641,025

[22] Filed: Jan. 14, 1991

Related U.S. Application Data

[62] Division of Ser. No. 542,564, Jun. 22, 1990, Pat. No. 5,009,699.

[51] Int. Cl.$^5$ .............................. C07C 225/22
[52] U.S. Cl. .................................... 564/305
[58] Field of Search ......................... 564/305

[56] References Cited

U.S. PATENT DOCUMENTS 3,647,890 3/1972 Kreevoy et al. ............ 564/305 X

Primary Examiner—Richard L. Raymond
Attorney, Agent, or Firm—Peggy A. Climenson

[57] ABSTRACT

This invention relates to a crop-selective, herbicidal agent 1-{[o-(cyclopropylcarbonyl)phenyl]sulfamoyl{-3-(4,6-dimethoxy-2-pyrimidinyl)urea, a method for the preparation thereof and a method for selectively controlling undesirable plant species in the presence of crops with the crop-selective sulfamoyl urea derivative.

1 Claim, No Drawings

0-AMINOPHENYL CYCLOPROPYL KETONE INTERMEDIATE

This is a divisional of co-pending application Ser. No. 07/542,564 filed on June 22, 1990, now U.S. Pat. No. 5,009,699.

BACKGROUND OF THE INVENTION

Sulfamoyl urea derivatives are described in U.S. Pat. Nos. 4,622,065, 4,666,508, 4,696,695 and 4,741,762. The sulfamoyl urea derivatives disclosed therein demonstrate herbicidal activity but do not provide a showing of selective weed control in the presence of crops.

It is therefore, an object of this invention to provide a 1-{[o-(cycloalkylcarbonyl)phenyl]sulfamoyl}-3-(4,6-dialkoxy-2-pyrimidinyl)urea derivative that is a highly effective herbicidal agent useful for the selective control of undesirable plant species in the presence of crops.

It is also an object of this invention to provide a crop selective 1-{[o-(cycloalkylcarbonyl)phenyl]sulfamoyl}-3-(4,6-dialkoxy-2-primidinyl)urea herbicide that exhibits at least a 2× margin of safety when applied to broadleaf weeds and grasses growing in the presence of cereal grains such as barley, wheat, oats, rye and upland rice and at least at 4× margin of safety when used for the control of broadleaf weeds and sedges in the presence of transplanted paddy rice.

It is another object of this invention to provide a method for selectively controlling undesirable vegetation in the presence of cereal grains utilizing 1-{[o-(cyclopropylcarbonyl)phenyl]sulfamoyl}-3-(4,6-dimethoxy-2-pyrimidinyl)urea. Among the undesirable weed species controlled by the above-named sulfamoyl urea are sicklepod, *Cassia obtusifolia*; annual sedges, *Cyperaceae annual*; yellow nutsedge, *Cyperus esculentus*; flatsedge, *Cyperus serotinus*; arrowhead, *Sagittaria pygmaea*; purple nutsedge, *Cyperus rotundus*; bulrush, Scirpus spp.; morningglory, Ipomoea spp. and hemp, *Sesbania exalta*.

SUMMARY OF THE INVENTION

The present invention relates to the preparation of 1-{[o-(cyclopropylcarbonyl)phenyl]sulfamoyl}-3-(4,6-dimethoxy-2-pyrimidinyl)urea and a method for the selective control of undesirable plant species in the presence of crops. It has been found that the above-said compound is effective for the selective control of a variety of weed species in the presence of cereal crops and is especially useful for controlling broadleaf weeds and sedges in the presence of transplanted or paddy rice.

Additionally, it has been found that this compound 1-{[o-(cyclopropylcarbonyl)phenyl]sulfamoyl}-3-(4,6-dimethoxy-2-pyrimidinyl)urea is unique amongst sulfamoyl urea derivatives in its superior margin of safety toward crop plants, especially rice plants and particularly transplanted paddy rice plants.

In accordance with the invention, 1-{[o-(cyclopropylcarbonyl)phenyl]sulfamoyl}-3-(4,6-dimethoxy-2-pyrimidinyl)urea may be prepared by the reaction of 2-amino-4,6-dimethoxypyrimidine with chlorosulfonyl isocyanate in the presence of methylene chloride followed by treatment of thus prepared reaction mixture with o-aminophenyl cyclopropyl ketone and triethylamine in the presence of methylene chloride, to yield the desired compound.

The discovery that the selectivity in cereal grains, particularly rice, is obtained by the introduction of a cyclopropyl group on the carboxyl function attached to the phenyl ring of a sulfamoyl urea derivative is unexpected. Moreover, the finding that this substitution also provides selective control of a variety of undesirable weeds, especially broadleaf weeds and sedges, in the presence of barley, wheat, oats and rye as well as rice, is surprising. Additionally, it is most advantageous to find that the development and/or maturation of several undesirable grass plants, such as barnyardgrass and quackgrass, are severely retarded, if they are not killed, when such grasses come in contact with 1-{[o-(cyclopropylcarbonyl)phenyl]sulfamoyl}-3-(4,6-dimethoxy-2-pyrimidinyl)urea during crop treatment for control of broadlead weeds and sedges in the presence of cereal crops.

In practice, the above-said sulfamoyl urea may be applied to crops in the form of a solid or liquid herbicidal composition, comprising a herbicidally effective amount of the sulfamoyl urea dispersed in an inert solid or liquid carrier. The formulations may be applied as preemergence or postemergence treatments. However, for rice treatments it is generally most effective to apply the above-said formulations preferably the granular formulations, as post transplant preemergence treatments, i.e. applied to the soil or to the flood water after the rice has been transplanted, but prior to or shortly after the emergence of weeds. The formulations may also be applied as preplant incorporated treatments.

The above-said formulations may also be applied as foliar applications to the cereal crops after the weeds have emerged, rendering them eminently suitable for use in weed control in barley, wheat, oats, rye and direct-seeded rice.

Advantageously 1-{[o-(cyclopropylcarbonyl)phenyl]sulfamoyl)}-3-(4,6-dimethoxy-2-pyrimidinyl)urea can be formulated as a wettable powder, liquid flowable or granular formulation useful for application to the crops in which weeds are to be controlled.

The wettale powder may be prepared by grinding together about 65% w/w of 1-}[o-(cyclopropylcarbonyl)phenyl]sulfamoyl}-3-(4,6-dimethoxy-2-pyrimidinyl)urea; about 25.07% w/w of bentonite clay; about 6.0% w/w of sugar free sodium based sulfonates of modified kraft lignin (dispersant); about 3.0% w/w of an anionic surfactant such as diocytyl sodium sulfosuccinate (wetting agent); about 0.20% w/w of silicon dioxide and about 0.10% w/w of a silicon anti-foam agent.

For application of this wettable powder to the crops and the weeds growing among the crops, the wettable powder is generally dispersed in water and applied as an aqueous spray thereto. Generally, the application of a sufficient quantity of spray to provide about 0.016 to 1.0 kg/ha and preferably about 0.02 to 0.20 kg/ha of the above-said 1-{[o-(cyclopropylcarbonyl)phenyl]sulfamoyl}-3-(4,6-dimethoxy-2-pyrimidinyl)urea is satisfactory for selectively controlling undesirable vegetation, particularly broadleaf weeds and sedges, in the presence of cereal grains.

The above-said sulfamoyl urea derivative may also be prepared as a granular formulation by dissolving or dispersing the active compound in a solvent such as acetone, methylene chloride or the like and applying the toxicant solvent mixture to sorptive granules such as attapulgite, montmorillonite, corn cob grits, bentonite or the like. Generally, sufficient toxicant solution is applied to the granules to provide from about 0.20% w/v to 2.0% of toxicant in the granule. Higher concentrations of toxicant on the granules can, of course, be prepared if desired. Sorptivity of the granules used is the major limiting factor. The granules are usually applied to the soil or water in which the crops are growing, in sufficient amount to provide about 0.016 to 1.0 kg/ha and preferably about 0.02 to 0.20 kg/ha of toxicant to the treated crops area.

A typical flowable concentrate formulation can be prepared by grinding together about 20% to 60% by weight of the sulfamoyl urea, about 1% to 5% by weight of the sodium salt of condensed naphthalene sulfonic acids, about 2% to 4% by weight of a gelling clay, about 2% by weight of propylene glycol and about 30% to 55% by weight of water.

The flowable concentrate is generally dispersed in water for application to the crop area in sufficient amount to provide the treated area with about 0.016 kg/ha to 1.0 kg/ha and preferably about 0.02 kg/ha to about 0.20 kg/ha.

The invention is further illustrated by the examples set forth below.

EXAMPLE 1

Preparation of o-aminophenyl cyclopropyl ketone

To 100 mL of a 1.0M BCl$_3$ solution in methylene chloride and 100 mL of ethylene dichloride is added 9.3 g (0.1 moles) of aniline at 0°–5° C. Following the addition of aniline, 10.0 g (0.15 mole) of cyclopropyl cyanide is added to the mixture and thereafter 14.4 g (0.11 mole) AlCl$_3$ is added portionwise thereto. The mixture is allowed to warm to room temperature and placed in a distillation unit. Methylene chloride is removed by distillation from the mixture until the pot temperature reaches 70° C. The remaining mixture is then refluxed overnight (18 hours).

The reaction mixture is cooled in an ice bath and water is added to the cooled mixture. Enough water is added to dissolve the solids in the mixture and then the entire mixture is extracted twice with 100 mL of methylene chloride. The organic extracts are combined, dried over anhydrous MgSO$_4$ and evaporated in vacuo to leave 9.3 g of yellow oil (70% real product) by NMR. The reaction is illustrated as follows:

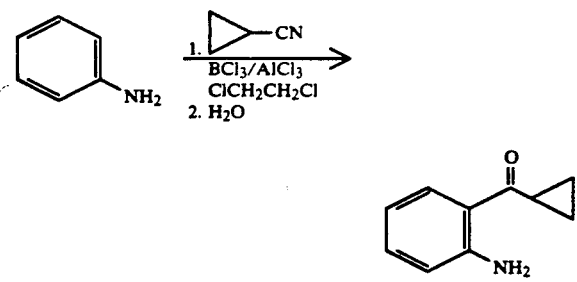

EXAMPLE 2

Preparation of 1-{[o-cyclopropylcarbonyl)phenyl]sulfamoyl}-3-(4,6-dimethoxy-2-pyrimidinyl)urea A solution of 1.78 g (0.0114 mole) of 2-amino-4,6-dimethoxypyrimidine in 50 mL of methylene chloride is cooled to 0.5° C. in an ice bath and 1.0 mL (1.62 g, 0.114 mole) of chlorosulfonyl isocyanate then added to the solution. The resulting mixture is stirred for 30 minutes and a solution of 2.66 g o-aminophenyl cyclopropyl ketone (70% real, 0.0114) and 2.6 mL triethylamine (0.0187 mole) in 50 mL of methylene chloride then slowly added to the mixture. The resulting solution is stirred at ambient temperature overnight (18 hours).

The reaction mixture is then evaporated in vacuo and the resulting residue dissolved in 50 mL of methanol. The pH of the resulting solution is adjusted to about pH 1 with 10% HCl and the solution permitted to stand. A white solid precipitate forms in the solution and is filtered and dried to give 3.8 g (70%) of the desired product, mp 170°–171° C. The reaction may be illustrated as follows:

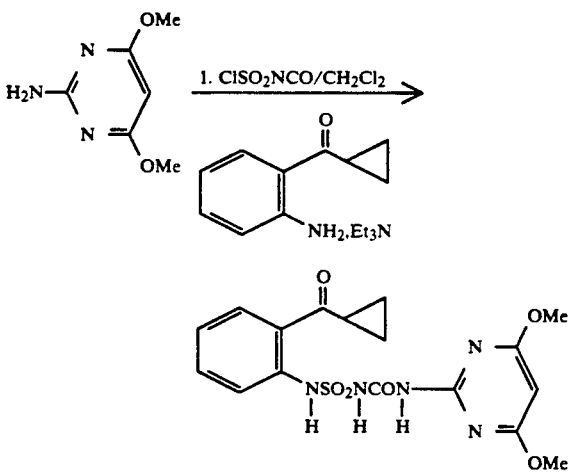

EXAMPLE 3

Preemergence rice tolerance under upland conditions

The preemergence rice tolerance to the compound of the present invention is exemplified by the following test in which rice seeds (cv Tebonnet) are planted in a steam pasteurized sassafras sandy loam soil with 1.5% organic matter in 4-inch square plastic pots with three replications. After planting, the pots are watered to field capacity and then sprayed with a laboratory belt sprayer. The test compound is applied as an aqueous acetone mixture 50/50 v/v at rates equivalent to 1.0, 0.5, 0.25, 0.125, 0.063, 0.032, 0.016 and 0.008 kg/ha. The treated pots are then placed on greenhouse benches watered and cared for according to normal greenhouse procedures. Three to four weeks after treatment each container is examined and rates for herbicidal effect based on visual determination of stand, size, vigor, chlorosis, growth malformation and over-all plant appearance. The rating system used is as follows:

| Rating | Meaning | % Control (compared to check) |
| --- | --- | --- |
| 0 | No effect | 0 |
| 1 | Trace effect | 1–5 |
| 2 | Slight effect | 6–15 |
| 3 | Moderate effect | 16–29 |
| 4 | Injury | 30–44 |
| 5 | Definite injury | 45–64 |
| 6 | Herbicidal effect | 65–79 |
| 7 | Good herbicidal effect | 80–90 |
| 8 | Approaching complete kill | 91–99 |
| 9 | Complete kill | 100 |

In this example the following abbreviations are used in the reported results.

| Abbreviation | Identity |
|---|---|
| PE | Preemergence |
| POST-T | Post-transplant |
| BYG | Barnyardgrass |
| CYPSE | *Cyperus serotinus* |
| G/HA | grams per hectare |
| KG/HA | kilograms per hectare |

Results of this test are reported below.

| Rice Selectivity (Preemergence) | | |
|---|---|---|
| Compound | Rate kg/ha | Herbicide rating |
| 1-{[o-(cyclopropylcarbamoyl)-phenyl]sulfamoyl}-3-(4,6-dimethoxy-2-pyrimidinyl)urea | 1.00 | 7 |
| | 0.50 | 7 |
| | 0.25 | 5 |
| | 0.125 | 1 |
| | 0.063 | 0 |
| | 0.032 | 0 |
| | 0.016 | 0 |
| | 0.008 | 0 |

Rice tolerance to post-transplant applications under flooded paddy conditions

The tolerance of transplanted rice to post-transplanted herbicide applications is determined as follows: Two ten-day-old rice seedlings (CV. Tebonnet) are transplanted into a silt loam soil in 32 oz plastic containers with a diameter of 10.5 cm and no drainage holes. After transplanting the containers are flooded and water level is maintained at 1.5 to 3 cm above the soil surface. Three days after transplanting, the flooded soil surface of the containers is treated with the selected aquaeous/acetone 50/50 v/v mixture containing the test compounds to provide the equivalent of 1.0, 0.5, 0.25, 0.125, 0.063, 0.032, 0.016 and 0.008 kg/ha of active ingredient. The treated containers are placed on greenhouse benches, watered such that water level is maintained as stated above, and cared for according to normal greenhouse procedures. Three to four weeks after treatment the test is terminated and each container is examined and herbicidal effect rated according to the above-noted rating system.

| PADDY CONDITIONS - POST-TRANSPLANT APPLICATIONS | | | | |
|---|---|---|---|---|
| Compound | Kg/ha | BYG | CYPSE | RICE |
| 1-{[o-(cyclopropyl-carbonyl)phenyl]-sulfamoyl-3-(4,6-dimethoxy-2-pyrimidinyl)urea | 1.00 | 9 | 9 | 3 |
| | 0.50 | 9 | 9 | 1 |
| | 0.125 | 9 | 9 | 0 |
| | 0.063 | 8 | 9 | 0 |
| | 0.032 | 8 | 8 | 0 |
| | 0.016 | 5 | 8 | 0 |
| | 0.008 | 2 | — | 0 |

Preemergence Weed Control Under Flooded Paddy Conditions

Preemergence herbicidal activity under flooded paddy conditions on barnyardgrass and *Cyperus serotinus* is determined as follows: Barnyardgrass seeds or *Cyperus serotinus* tubers are planted in the top 0.5 cm of silt loam soil in 32 oz plastic containers with a diameter of 10.5 cm and no drainage holes. Water is added to these containers and maintained at 1.5 to 3 cm of above the soil surface for the duration of the experiment. The test compounds are applied as an aqueous/acetone mixture 50/50 v/v pipetted directly into the flood water to give the equivalent of 1.0, 0.5, 0.25, 0.125, 0.063, 0.032, 0.016 and 0.008 kg/ha of active ingredient. The treated containers are placed on greenhouse benches and cared for according to normal greenhouse procedures. Three to four weeks after treatment the test is terminated and each container is examined and herbicidal effect rated according to the above-noted rating system.

Rice Safe Rate and Weed Control Rate

Rice safe rate is the highest rate (in g/ha) with a rice herbicide rating of 0 to 1. Weed control rate is the lowest rate in g/ha with a herbicide rating of 8 or 9.

| Compound | Rice Safe Rate PE | Rice Safe Rate Post-T | BYG Control Rate | CYPSE Control Rate |
|---|---|---|---|---|
| | | - (G/ha) - | | |
| 1-{[o-(cyclopropyl-carbonyl)phenyl]-sulfamoyl}-3-(4,6-dimethoxy-2-pyrimidinyl)urea | 63 | 500 | 32 | 16 |

Selectivity Margins

Selectivity margin is race safe rate (g/ha) divided by weed control rate (g/ha) for each weed species (barnyardgrass and *Cyperus serotinus*). This is calculated using transplanted rice safe rates and again using preemergence rice safe rates. Although the PE rice planting method is not used under flooded paddy conditions, this is a more extreme method of evaluating physiological rice tolerance to these herbicides, as rice seedlings are exposed to the herbicides from time of seed germination.

| | Selectivity Margins | | | |
|---|---|---|---|---|
| | Rice Post-Transplant | | Rice PE | |
| Compound | Byg | CYPSE | BYG | CYPSE |
| 1-{[o-(cyclopropyl-carbonyl)phenyl]sulfamoyl}-3-(4,6-dimethoxy-2-pyrimidinyl)urea | 16 | 32 | 2.0 | 4 |

EXAMPLE 4

Weed control of broadleaf weeds and tolerance of wheat and barley postemergence

The postemergence herbicide activity and wheat and barley selectivity is demonstrated by the following tests. Seeds or propagating organs of each plant species are planted in separate cups, in a commercial artificial greenhouse growth media composed of peat moss, vermiculite, sand and charcoal (Metromix 350). Plants are grown in a greenhouse for about two weeks. The plants are then sprayed with the selected aqueous acetone solution containing test compound in sufficient quantity to provide the equivalent of about 0.004 to 2.0 kg/ha. These solutions also contain approximately 2 molar equivalents of diethylamine per molar equivalent of test compound, to add solubility of the test compound in the aqueous acetone solution. These solutions also contain 0.25% of a spreader activator such as alkylaryl polyoxyethylene glycol plus free fatty acid and isopropanol.

After spraying, the plants are placed on greenhouse benches and are cared for in the usual manner, commensurate with conventional greenhouse practices. Three to five weeks after treatment, each cup is examined and the herbicidal effect is rated according to the rating system reported in the previous example.

For the test of cereal tolerance, three pots are treated with each treatment, and data given represents average values for these three replications.

| Crop And Weed Species Employed In These Tests | | |
|---|---|---|
| Crops | | |
| Common Name And Variety | | Scientific Name |
| Rice cv. Tebonnet | | *Oryza sativa* |
| Barley, winter cv. Barberouse | | *Hordeum vulgare* |
| Barley, spring cv. Bonanza | | *Hordeum vulgare* |
| Wheat, winter cv. Fidel | | *Triticum aestivum* |
| Wheat, spring cv. Katepwa | | *Triticum aestivum* |
| Wheat, durum cv. Wakooma | | *Triticum aestivum* |
| Weed Species | | |
| Abbreviation | Common Name | Scientific Name |
| BYG | Barnyardgrass | *Echinochloa crus-galli* |
| CYPSE | Flatsedge | *Cyperus serotinus* |
| GALAP | Galium | *Galium aparine* |
| STEME | Chickweed | *Stellaria media* |
| TAROF | Dandelion | *Taraxacum officinale* |
| KCHSC | Kochia | *Kochia scoparia* |
| VIOAR | Field violet | *Viola arvensis* |
| PAPSS | Poppy | *Papaver sp.* |
| MATIN | Mayweed | *Matricaria inodora* |
| PRUVS | Healall | *Prunella vulgaris* |
| VERSS | Speedwell | *Veronica sp.* |

Tolerance Of Cereal Species And Varieties To Postemergence Applications of 1{[o-(cyclopropylcarbonyl)phenyl]sulfamoyl}-3-(4,6-dimethoxy-2-pyrimidinyl)urea
Visual Herbicide Rating According To The Rating System Reported Above

| kg/ha | Winter barley 'Barberouse' | Winter wheat 'Fidel' | Durum wheat 'Wakooma' | Spring wheat 'Katepwa' | Spring barley 'Bonanza' |
|---|---|---|---|---|---|
| 2.00 | 5.3 | 3.7 | 3.7 | 4.0 | 5.3 |
| 1.00 | 4.0 | 2.7 | 3.0 | 2.3 | 4.3 |
| 0.500 | 3.7 | 2.7 | 2.3 | 2.0 | 4.0 |
| 0.250 | 2.3 | 1.7 | 0.7 | 1.7 | 3.7 |
| 0.125 | 1.7 | 1.0 | 0.0 | 1.3 | 2.7 |
| 0.063 | 0.7 | 0.0 | 0.3 | 0.0 | 1.3 |
| 0.032 | 0.3 | 0.0 | 0.0 | 0.0 | 0.3 |

Control Of Weed Species Via Postemergence Application of 1-{[o-(cyclopropylcarbonyl)phenyl]sulfamoyl}-3-(4,6-dimethoxy-2-pyrimidinyl)urea
Using The Rating System Of Example 3

| Rate kg/ha | GALAP | STEME | TAROF | KCHSC | VIOAR | PAPSS | MATIN | PRUVA | VERSS |
|---|---|---|---|---|---|---|---|---|---|
| 0.125 | 9 | 0 | 9 | 4 | 0 | 6 | 9 | 9 | 9 |
| 0.063 | 9 | 0 | 9 | 3 | 0 | 8 | 8 | 9 | 7 |
| 0.032 | 9 | 0 | 5 | 0 | 0 | 6 | 9 | 9 | 3 |
| 0.016 | 8 | 0 | 4 | 0 | 0 | 6 | 9 | 9 | 3 |
| 0.008 | 7 | 0 | 4 | 0 | 0 | 4 | 7 | 9 | 0 |
| 0.004 | 4 | 0 | 0 | 0 | 0 | 2 | 5 | 8 | 0 |

We claim:
1. o-aminophenyl cyclopropyl ketone.

* * * * *